United States Patent [19]

Zambounis et al.

[11] Patent Number: 5,527,922
[45] Date of Patent: Jun. 18, 1996

[54] PYRROLO[3,4-C]PYRROLES CONTAINING CYANIMINO GROUPS

[75] Inventors: John S. Zambounis, Murten; Zhimin Hao, Marly; Abul Iqbal, Arconciel, all of Switzerland

[73] Assignee: Ciba-Geigy Corporation, Tarrytown, N.Y.

[21] Appl. No.: 407,746

[22] Filed: Mar. 21, 1995

[30] Foreign Application Priority Data

Mar. 25, 1994 [CH] Switzerland ............................... 915/94

[51] Int. Cl.$^6$ ................................................. C07D 487/04
[52] U.S. Cl. ........................ 548/453; 548/181; 548/215; 546/199; 546/256; 546/270.1; 546/271.7; 546/273.4; 546/272.7; 546/275.4; 546/271.4; 546/272.4; 546/276.7; 546/193; 546/194; 546/200; 546/198; 544/153; 544/373
[58] Field of Search ..................... 548/453, 181, 548/215; 546/271, 199; 544/153, 373

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,585,878 | 4/1986 | Jost et al. | 548/453 |
| 5,017,706 | 5/1991 | Rochat et al. | 548/414 |

FOREIGN PATENT DOCUMENTS 0133156  2/1985  European Pat. Off. .

OTHER PUBLICATIONS

S. Hunig et al., Angew Chem. 96, 437 (1984).
S. Hunig, et al., Angew Chem. 102, 220 (1990).

Primary Examiner—David B. Springer
Attorney, Agent, or Firm—Michele A. Kovaleski

[57] ABSTRACT

The invention relates to pyrrolo[3,4-c]pyrroles of formula $$\text{(I)}$$

wherein D and E are each independently of the other hydrogen, $C_1$–$C_{18}$alkyl, $C_2$–$C_4$alkenyl, $C_7$–$C_{10}$aralkyl, unsubstituted phenyl or phenyl which is substituted by chloro, bromo, $C_1$–$C_6$alkyl, $C_1$–$C_4$alkoxy, trifluoromethyl or nitro, or —COO—$C_1$–$C_5$alkyl or a group —COOR$_8$, wherein R$_8$ is benzyl, piperidyl or a group and
X and Y are N—CN or O, with the proviso that at least one of X or Y N—CN must be N—CN.

These pyrrolo[3,4-c]pyrroles are preeminently suitable for use as colorants, i.e. as pigments or as polymer-soluble dyes, for colouring high molecular weight organic material. They are distinguished by unexpectedly high solid-state fluorescence.

The substituents A and B are as defined in claim 1.

7 Claims, No Drawings

PYRROLO[3,4-C]PYRROLES CONTAINING CYANIMINO GROUPS

The present invention relates to novel 1-keto-4-cyaniminopyrrolo[3,4-c]pyrroles and 1,4-dicyaniminopyrrolo [3,4-c]pyrroles, to a process for their preparation and to the use thereof for colouring organic material of high molecular weight.

1,4-Diketopyrrolo[3,4-c]pyrroles have been known for some years and are disclosed as useful pigments, inter alia, in U.S. Pat. Nos. 4,415,685 and 4,579,949. A number of these pigments have found acceptance in practice as high-performance pigments. N-Substituted 1,4-diketopyrrolo[3,4-c]pyrroles which, depending on the nature of their substituents, can be used as polymer-soluble dyes or as pigments, are disclosed in U.S. Pat. No. 4,585,878. When these compounds are dissolved in the polymers used as substrates, they also exhibit, inter alia, high fluorescence. However, the N-unsubstituted 1-keto-4-iminopyrrolo[3,4-c]pyrroles disclosed in U.S. Pat. No. 5,017,706 also have the same properties.

The invention provides novel 1-keto-4-cyaniminopyrrolo[3,4-c]pyrroles and 1,4-dicyaniminopyrrolo[3,4-c]pyrroles having surprisingly good properties which make them pre-eminently suitable for use as colorants, i.e. as pigments or as polymer-soluble dyes, for colouring organic material of high molecular weight. These novel compounds obtained by replacement of the keto group with the cyanimino group or with cyanimino groups are characterised, inter alia, by a bathochromic change in shade and, very surprisingly, by a high solid-state fluorescence.

Accordingly, the invention relates to pyrrolo[3,4-c]pyrroles of formula

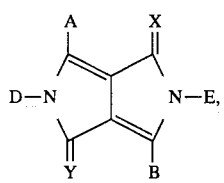

(I)

wherein A and B are each independently of the other a group of formula

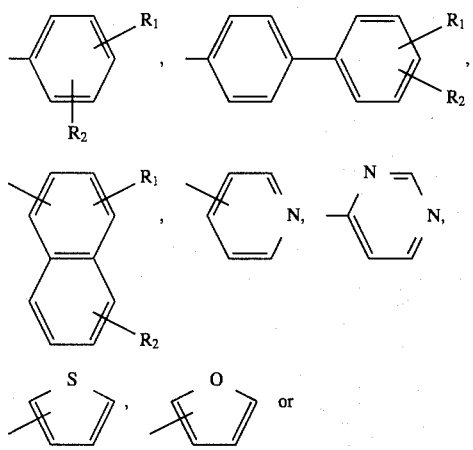

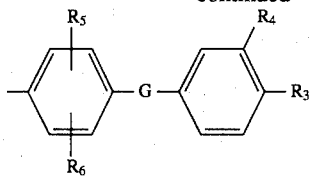

wherein $R_1$ and $R_2$ are each independently of the other hydrogen, halogen, $C_1-C_{18}$alkyl, $C_1-C_{18}$alkoxy, $C_1-C_{18}$alkylmercapto, $C_1-C_{18}$alkylamino, —CN, —NO$_2$, phenyl, trifluoromethyl, $C_5-C_6$cycloalkyl, —C≡N—($C_1-C_{18}$alkyl),

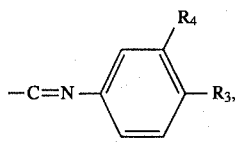

imidazolyl, pyrazolyl, triazolyl, piperazinyl, pyrrolyl, oxazolyl, benzoxazolyl, benzothiazolyl, benzimidazolyl, morpholinyl, piperidinyl or pyrrolidinyl, $R_3$ and $R_4$ are each independently of the other hydrogen, halogen, $C_1-C_6$alkyl, $C_1-C_{18}$alkoxy or —CN, $R_5$ and $R_6$ are each independently of the other hydrogen, halogen or $C_1-C_6$alkyl, and G is —CH$_2$—, —CH(CH$_3$)—, —(CH$_3$)$_2$, —CH=N—, —N=N—, —O—, —S—, —SO—, —SO$_2$— or —NRT—, wherein $R_7$ is hydrogen or $C_1-C_6$alkyl, D and E are each independently of the other hydrogen, $C_1-C_{18}$alkyl, $C_2-C_4$alkenyl, $C_7-C_{10}$aralkyl, unsubstituted phenyl or phenyl which is substituted by chloro, bromo, $C_1-C_6$alkyl, $C_1-C_4$alkoxy, trifluoromethyl or nitro; —COO—$C_1-C_5$alkyl or a group —COOR$_8$, wherein $R_8$ is benzyl, piperidyl or a group

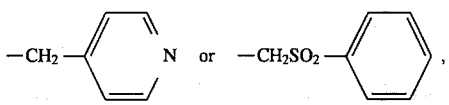

and X and Y are N—CN or O, with the proviso that at least one of X or Y must be N—CN.

Halogen substituents will be generally understood to mean iodo, fluoro, preferably bromo and, most preferably, chloro.

$C_1-C_6$Alkyl will typically be methyl, ethyl, n-propyl, isopropyl, n-butyl, sec-butyl, tert-butyl, n-amyl, tert-amyl, hexyl; and $C_1-C_{18}$alkyl will additionally be taken to mean heptyl, octyl, 2-ethylhexyl, nonyl, decyl, dodecyl, tetradecyl, hexadecyl or octadecyl.

$C_1-C_4$Alkoxy will typically be methoxy, ethoxy, n-propoxy, isopropoxy, butoxy; and $C_1-C_{18}$alkoxy will additionally be taken to mean hexyloxy, decyloxy, dodecyloxy, hexadecyloxy or octadecyloxy.

$C_1-C_{18}$Alkylmercapto will typically be methylmercapto, ethylmercapto, propylmercapto, butylmercapto, octylmercapto, decylmercapto, hexadecylmercapto or octadecylmercapto.

$C_1-C_{18}$Alkylamino is typically methylamino, ethylamino, propylamino, hexylamino, decylamino, hexadecylamino or octadecylamino.

$C_3-C_6$Cycloalkyl is typically cyclopropyl, cyclopentyl and, preferably, cyclohexyl.

$C_2-C_4$Alkenyl is typically vinyl, allyl, methallyl or 2-butenyl.

$C_7$–$C_{10}$Aralkyl is typically 1-phenethyl, 1,1-dimethylbenzyl which is substituted in the benzene nucleus by methyl or ethyl, or is preferably benzyl.

COO—$C_1$–$C_5$Alkyl is typically methoxycarbonyl, ethoxycarbonyl, isopropoxycarbonyl, n-butoxycarbonyl, tert-amyloxycarbonyl or, preferably, tert-butoxycarbonyl.

Particularly interesting pyrrolo[3,4-c]pyrroles of formula I are those wherein A and B are each independently of the other a group of formula

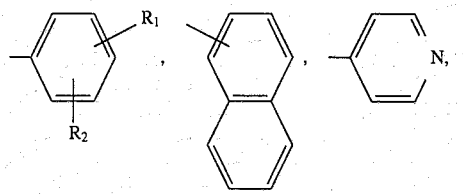

wherein $R_1$ and $R_2$ are each independently of the other hydrogen, chloro, bromo, $C_1$–$C_4$alkyl, $C_1$–$C_6$alkoxy, $CFC_6$alkylamino, CN or phenyl, $R_3$ and $R_4$ are hydrogen, and G is —O—, —$NR_7$—, —N=N— or —$SO_2$—, wherein $R_7$ is hydrogen, methyl or ethyl, and A and B are preferably identical, and especially those wherein A and B are a group of formula

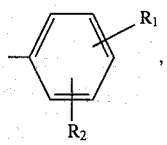

wherein $R_1$ and $R_2$ are each independently of the other hydrogen, methyl, tert-butyl, chloro, bromo, CN or phenyl. $R_2$ is preferably hydrogen.

Preferred pyrrolo[3,4-c]pyrroles of formula I are those wherein D and E are identical and are $C_1$–$C_4$alkyl, unsubstituted or chloro-substituted phenyl, allyl or benzyl, or a group

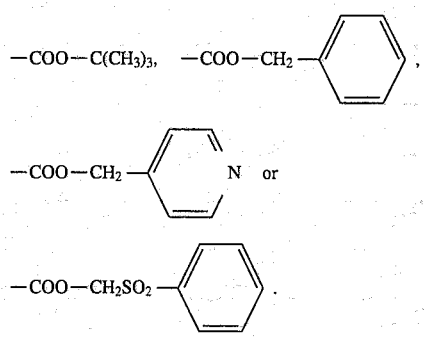

D and E are preferably $C_1$–$C_4$alkyl or a group —COO—$C(CH_3)_3$ and X and Y are the group N—CN.

The preparation of the novel pyrrolo[3,4-c]pyrroles of formula I, wherein A, B, X and Y are as defined above and D and E are each independently of the other hydrogen, $C_1$–$C_{18}$alkyl, $C_2$–$C_4$alkenyl, $C_7$–$C_{10}$aralkyl, unsubstituted phenyl or phenyl which is substituted by chloro, bromo, $C_1$–$C_6$alkyl, $C_1$–$C_4$alkoxy, trifluoromethyl or nitro, is carried out by a method analogous to one described by S. Hünig et al. in Angew. Chem. 96, 437, 1984 and 102, 220, 1990, very surprisingly in good yield, by reacting a pyrrolo[3,4-c]pyrrole of formula

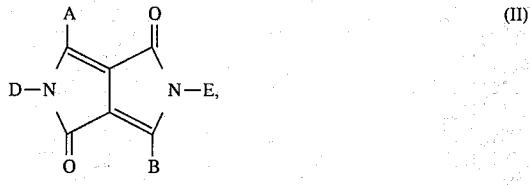

wherein A and B are as defined above and D and E have the meaning just given, in the desired molar ratio with a compound of formula

or

where $R_9$ is $C_1$–$C_6$alkyl, in the presence of a Lewis acid as catalyst and in an aprotic organic solvent, in the temperature range from 10° to 150° C., preferably from 50° to 100° C.

The reaction time will vary from about 30 minutes to about 200 hours, in accordance with the substituents.

The method described by Hünig et al. relates solely to the reaction of soluble starting materials. That the reaction would also be able to proceed so successfully starting from insoluble diketopyrrolo[3,4-c]pyrroles was not to be expected. Accordingly, the invention also relates to this novel process.

The compound III or IV supplying the cyanimino groups is preferably used in about a 10- to 20-fold excess, based on the pyrrolopyrrole. This excess is preferred.

A Lewis acid which may suitably be used as catalyst is typically CsF, $BF_3$, $ZrCl_4$ and, preferably, $TiCl_4$.

Suitable solvents are typically ethers such as tetrahydrofuran or dioxane, or glycol ethers such as ethylene glycol methyl ether, ethylene glycol ethyl ether, diethylene glycol monomethyl ether or diethylene glycol monoethyl ether; and also dipolar aprotic solvents such as acetonitrile, benzonitrile, N,N-dimethylformamide, N,N-dimethylacetamide, nitrobenzene, N-methylpyrrolidone, halogenated aliphatic or aromatic hydrocarbons such as trichloroethane, benzene or alkyl-, alkoxy- or halogen-substituted benzene, typically toluene, xylene, anisole or chlorobenzene; or aromatic N-heterocycles such as pyridine, picoline or quinoline. Preferred solvents are typically tetrahydrofuran, N,N-dimethylformamide, N-methylpyrrolidone. The cited solvents may also be used as mixtures. It is convenient to use 5–20 parts by weight of solvent to 1 part by weight of reactants.

Pyrrolo[3,4-c]pyrroles of formula II are known compounds. Any that are novel can be prepared by standard known methods. Pyrrolo[3,4-c]pyrroles of formula I, wherein D and/or E is —COO—$C_1$–$C_5$alkyl or a group —$COOR_8$, can be prepared by methods analogous to known ones, conveniently by reacting the pyrrolo[3,4-c]pyrrole of formula I, wherein D and E are hydrogen, in the desired molar ratio, with a dicarbonate of formula

or with a 1:1 mixture of dicarbonate of formula V and dicarbonate of formula $$D\text{—}O\text{—}D \qquad (VI),$$

wherein E and D are each independently of the other —COO—$C_1$–$C_5$alkyl or a group —COOR$_8$, wherein R$_8$ has the above meaning.

The compounds of formulae III, IV, V and VI are known compounds which are commercially available.

Depending on the nature of their substituents and of the polymers to be coloured, the pyrrolo[3,4-c]pyrroles of formula I, like the corresponding 1,4-diketopyrrolo[3,4-c]pyrroles disclosed in U.S. Pat. No. 4 585 878, can be used as polymer-soluble dyes for e.g. polystyrene, polyamides, ABS and, preferably, linear polyesters, or also as pigments for high-molecular weight organic material. Compared with the 1,4-diketopyrrolo[3,4-c]pyrroles, the pyrrolo[3,4-c]pyrroles of this invention are distinguished in particular by a surprisingly high solid-state fluorescence as well as by a coloristically interesting bathochromic change of shade.

Linear polyesters for the colouring of which the novel polymer-soluble pyrrolo[3,4-c]pyrroles are particularly suitable are preferably those which are obtained by the polycondensation of terephthalic acid or the esters thereof with glycols of formula HO—$(CH_2)_n$—OH, wherein n is 2–10, or with 1,4-bis(hydroxymethyl)cyclohexane, or by polycondensation of glycol ethers of hydroxybenzoic acids, typically p-(β-hydroxyethoxy)benzoic acid. The term "linear polyester" also embraces copolyesters which are obtained by partial replacement of the glycol by another diol. The polyethylene terephthalates, however, are of particular interest.

The linear polyesters to be coloured are thoroughly blended with the colorant in the form of powders, chips or granules. This can be typically done by coating the polyester particles with the finely powdered dry colorant powder or by treating the polyester particles with a solution or dispersion of the colorant in an organic solvent and subsequently removing the solvent.

To adjust the shade, mixtures of the pyrrolo[3,4-c]pyrroles of formula I and also mixtures of one or more than one compound of formula I with disperse dyes can be used.

Finally, the pyrrolo[3,4-c]pyrroles of formula I can also be added direct to the polyester melt or also before or during the polycondensation of the polyethylene terephthalate.

Depending on the desired colour strength, the ratio of colorant to polyester can vary over a wide range. It is normally desirable to use 0.01–3 parts of colorant to 100 parts of polyester.

The polyester particles so treated are fused by known methods in an extruder and compression moulded to objects, preferably sheets or filaments, or cast to boards.

For the utility as pigments, it is useful to convert the products obtained in the synthesis into a finely dispersed form. This can be done in a number of different ways, typically comprising:

a) By milling or kneading, conveniently in the presence of grinding assistants such as inorganic or organic salts with or without the addition of organic solvents. After milling, the assistants are removed in conventional manner: soluble inorganic salts e.g. with water and water-insoluble organic solvents e.g. by steam distillation.

b) By repreciptation from sulfuric acid, methanesulfonic acid, trichloroacetic acid or polyphosphoric acid.

c) In the case of products in which D and/or E are hydrogen, by convening the crude pigment into an alkali salt or amine salt and hydrolysing this latter. This may be done by stirring the crude pigment with a base, suitably an alkali metal hydroxide or alcoholate, ammonia or an amine, in a polar organic solvent such as dimethyl formamide, whereupon the pigment dissolves wholly or partially. The pigment is precipitated by hydrolysis, preferably by acidifying the non-filtered or filtered solution.

d) It can be useful to subject the pigments treated according to a), b) or c) to an aftertreatment with an organic solvent, preferably with one that has a boiling point above 100° C.

Particularly suitable solvents are benzenes which are substituted by halogen atoms, alkyl or nitro groups, typically xylenes, chlorobenzene, o-dichlorobenzene or nitrobenzene, as well as pyridine bases such as pyridine, picoline or quinoline; and also ketones such as cyclohexanone; ethers such as ethylene glycol monomethyl or monoethyl ether; amides such as dimethyl formamide or N-methylpyrrolidone; and dimethyl sulfoxide, sulfolane or water alone, under normal or elevated pressure. The aftertreatment can also be carded out in water or in the presence of an organic solvent and/or with the addition of surfactants, or aliphatic amines or with liquid ammonia.

Depending on the envisaged end use, it is advantageous to use the pigments as obtained (toners) or in the form of preparations.

The high molecular weight organic material can be of natural or synthetic origin. It may typically comprise natural resins or drying oils, rubber or casein or modified natural substances such as chlorinated rubber, oil-modified alkyd resins, viscose, cellulose ethers and esters, including cellulose acetate, cellulose propionate, cellulose acetobutyrate or nitrocellulose, but preferably comprises man-made organic polymers (thermosetting resins and thermoplastic resins) obtained by polymerisation, polycondensation or polyaddition. Polymers of the class of polymerisation resins are in particular: polyolefins, typically polyethylene, polypropylene or polyisobutylene, and substituted polyolefins, including polymers of vinyl chloride, vinyl acetate, styrene, acetonitrile, acrylates and/or methacrylates or butadiene, as well as copolymers of the cited monomers, preferably ABS or EVA.

Polymers of the class of polyaddition resins and polycondensation resins are typically the condensates of formaldehyde with phenols, i.e. phenolic plastics, and the condensates of formaldehyde with urea, thiourea and melamine, i.e. aminoplastics, the polyesters used as surface-coating resins, viz. saturated polyesters such as alkyd resins, as well as unsaturated polyesters such as maleate resins, and also the linear polyesters, polycarbonates, polyurethanes and polyamides or silicones.

The aforementioned high molecular weight materials may be singly or in mixtures in the form of plastics materials or of melts which may be spun to fibres.

They may also be in the form of their monomers or in the polymerised state in dissolved form as film formers or binders for paints and varnishes or printing inks, for example boiled linseed oil, nitrocellulose, alkyd resins, melamine resins and urea/formaldehyde resins, or acrylic resins.

The pigmenting of the high molecular weight organic materials with the pigments of formula (I) is conveniently effected by incorporating such a pigment by itself or in the form of a masterbatch in the substrates using roll mills, mixing or milling apparatus. The pigmented material is then brought into the desired final form by methods which are known per se, conveniently by calendering, moulding, extruding, coating, casting or by injection moulding. It is often desirable to incorporate plasticisers into the high molecular weight compounds before processing in order to produce non-brittle mouldings or to diminish their brittleness. Suitable plasticisers are typically esters of phosphoric acid, phthalic acid or sebacic acid. The plasticisers may be incorporated before or after blending the pigments of this invention into the polymers. To obtain different shades it is also possible to add fillers or other chromophoric components such as white, coloured or black pigments in any amount to the high molecular weight organic materials in addition to the pyrrolo[3,4-c]pyrroles of formula (I).

For pigmenting paint systems and printing inks, the high molecular weight organic materials and the pyrrolo[3,4-c]pyrroles of formula (I), together with optional additives such as fillers, other pigments, siccatives or plasticisers, are finely dispersed or dissolved in a common organic solvent or mixture of solvents. The procedure may be such that the individual components by themselves, or also several components together, are dispersed or dissolved in the solvent and thereafter all the components are mixed.

The colorations obtained, typically in plastics, filaments, paint systems or printing inks, have a yellow to red shade, very high colour strength, high saturation, good dispersibility, good fastness to overspraying, migration, heat, light and weather, as well as good gloss and good IR remission. As already mentioned, very characteristic of the pyrrolo[3,4-c]pyrroles of formula (I) is their surprisingly high solid-sate fluorescence.

The pyrrolo[3,4-c]pyrroles of formula (I) can also be used as toners for electrography and magnetography. They may also be used as colorants for printing inks, especially for ink jet printing and safety printing.

When the pyrrolo[3,4-c]pyrroles of formula (I) are dissolved in the polymers employed, they are also distinguished by a pure hue, superior colour strength, good fastness properties, especially fastness to light and sublimation, and also by high fluorescence. They are suitable for use in solar energy collectors and for the induction of laser beams. Furthermore, they are very suitable for use as organic photoconductors for copying machines and laser printers as well as active components of electroluminescence elements.

The invention is illustrated by the following Examples.

EXAMPLE 1

A solution of 14.48 ml (64 mmol) of bis(trimethylsilyl)carbodiimide in 30 ml of 1,2-dichlorobenzene is added, under argon, to a solution of 7.03 ml (64 mmol) of $TiCl_4$ in 30 ml of 1,2-dichlorobenzene. After 30 minutes, a suspension of 1.5 g (3.2 mmol) of N,N'-dimethyl-1,4-diketo-3,6-diphenylpyrrolo[3,4-c]pyrrole in 30 ml of 1,2-dichlorobenzene is added to the resultant red solution. The dark brown suspension is stirred for 8 days at 80° C. and afterwards poured into 400 g of ice-water. The precipitate is then isolated by filtration, washed with water and then with acetone and dried in the air. The red powder is recrystallised from 700 ml of benzonitrile at 155° C. The crystalline product is isolated by filtration and washed with benzonitrile, affording 1.105 g (67%) of N,N'-dimethyl-1,4-di-cyanimino-3,6-diphenylpyrrolo[3,4-c]pyrrole in the form of a bordeaux-red fluorescent powder with a melting point of 328.6° C.

UV (benzonitrile): $\lambda_{max}$ 530 nm.

| Analysis: | C | H | N |
|---|---|---|---|
| calculated: | 79.05% | 4.68% | 16.27% |
| found: | 76.53% | 4.77% | 16.17% |

EXAMPLES 2–14

Following the procedure described in Example 1, the corresponding amount of 1,4-diketo-pyrrolo[3,4-c]-pyrrole is reacted with the desired amount of bis(trimethylsilyl)carbodiimide in accordance with the following scheme to give the products listed in Table 1.

The amounts of starting materials, $\lambda_{max}$ and m.p. are shown for the respective Examples in Table 2.

TABLE 1

$$\text{[1,4-Diketopyrrolopyrrole structure]} \xrightarrow[\text{TiCl}_4]{(CH_3)_3Si-N=C=N-Si(CH_3)_3} \text{[Carbodiimide product structure]}$$

| Example | R₁ | R₂ | R₃ | D | E | X | Y | 1,4-Diketopyrrolopyrrole | Carbodiimide | λmax/CH₂Cl₂ | m.p. |
|---|---|---|---|---|---|---|---|---|---|---|---|
| 2 | H | H | H | —CH₃ | —CH₃ | O | N—CN | 12.64 mmol | 126.4 mmol | 491 nm | 205.6° C. |
| 3 | H | H | H | —CH₂CHCH₂ | —CH₂CHCH₂ | O | N—CN | 1.36 mmol | 13.6 mmol | 488 nm | 169.3° C. |
| 4 | H | H | H | —CH₂CHCH₂ | —CH₂CHCH₂ | N—CN | N—CN | 1.36 mmol | 13.6 mmol | 513 nm | 227.6° C. |
| 5 | H | H | H | —CH₂CH₃ | —CH₂CH₃ | O | N—CN | 16.06 mmol | 160.5 mmol | 488 nm | 259.4° C. |
| 6 | H | H | t-butyl | —CH₂CH₃ | —CH₂CH₃ | N—CN | N—CN | 16.06 mmol | 160.5 mmol | 514 nm | 326.8° C. |
| 7 | H | H | t-butyl | —CH₃ | —CH₃ | O | N—CN | 1.16 mmol | 11.6 mmol | 495 nm | 305.8° C. |
| 8 | H | H | Cl | —CH₃ | —CH₃ | N—CN | N—CN | 1.16 mmol | 11.6 mmol | 520 nm | dec. 387° C. |
| 9 | H | H | Br | —CH₃ | —CH₃ | N—CN | N—CN | 3.9 mmol | 78 mmol | 524 nm | dec. 361° C. |
| 10 | H | H | H | —CH₃ | —CH₃ | N—CN | N—CN | 2.2 mmol | 42.2 mmol | 524 nm | dec. 368° C. |
| 11 | OCH₃ | H | H | —CH₃ | —CH₃ | O | N—CN | 1.22 mmol | 13.3 mmol | 487 nm | 179.4° C. |
| 12 | OCH₃ | H | Cl | —CH₃ | —CH₃ | N—CN | N—CN | 1.22 mmol | 13.3 mmol | 520 nm | dec. 283° C. |
| 13 | H | H | phenyl | —CH₂CHC(CH₃)₂ | —CH₂CHC(CH₃)₂ | N—CN | N—CN | 0.41 mmol | 4.1 mmol | 521 nm | 262.3° C. |
| 14 | H | H | H | —CH₂CHC(CH₃)₂ | —CH₂CHC(CH₃)₂ | N—CN | N—CN | 2.27 mmol | 9.08 mmol | 521 nm | 260.9° C. |
| 15 | H | H | H | -phenyl | -phenyl | N—CN | N—CN | 1.12 mmol | 11.2 mmol | 444 nm | 170° C. |
| 16 | H | H | H | —CH₂-phenyl | —CH₂-phenyl | N—CN | N—CN | 2.5 mmol | 25 mmol | 430 nm | 272° C. |

What is claimed is:

1. A pyrrolo[3,4-c]pyrrole of formula $$\begin{array}{c} A \quad\quad X \\ D-N \quad\quad N-E, \\ Y \quad\quad B \end{array} \quad (I)$$

wherein A and B are each independently of the other a group of formula

[structures shown with $R_1$, $R_2$; biphenyl with $R_1$, $R_2$; naphthyl with $R_1$, $R_2$; pyridyl; pyrimidyl N; thienyl S; furyl O; and phenyl-G-phenyl with $R_3$, $R_4$, $R_5$, $R_6$]

wherein $R_1$ and $R_2$ are each independently of the other hydrogen, halogen, $C_1$–$C_8$alkyl, $C_1$–$C_{18}$alkoxy, $C_1$–$C_{18}$alkylmercapto, $C_1$–$C_{18}$alkylamino, —CN, —NO$_2$, phenyl, trifluoromethyl, $C_5$–$C_6$cycloalkyl, —C=N—($C_1$–$C_{18}$alkyl),

[structure: —C=N— with phenyl bearing $R_3$, $R_4$]

imidazolyl, pyrazolyl, triazolyl, piperazinyl, pyrrolyl, oxazolyl, benzoxazolyl, benzothiazolyl, benzimidazolyl, morpholinyl, piperidinyl or pyrrolidinyl, $R_3$ and $R_4$ are each independently of the other hydrogen, halogen, $C_1$–$C_6$alkyl, $C_1$–$C_{18}$alkoxy or —CN, $R_5$ and $R_6$ are each independently of the other hydrogen, halogen or $C_1$–$C_6$alkyl, and G is —CH$_2$—, —CH(CH$_3$)—, —(CH$_3$)$_2$, —CH=N—, —N=N—, —O—, —S—, —SO—, —SO$_2$ or —NR$_7$—, wherein $R_7$ is hydrogen or $C_1$–$C_6$alkyl, D and E are each independently of the other hydrogen, $C_1$–$C_{18}$alkyl, $C_2$–$C_4$alkenyl, $C_7$–$C_{10}$aralkyl, unsubstituted phenyl or phenyl which is substituted by chloro, bromo, $C_1$–$C_6$alkyl, $C_1$–$C_4$alkoxy, trifluoromethyl or nitro; —COO—$C_1$–$C_5$alkyl or a group —COOR$_8$, wherein $R_8$ is benzyl, piperidyl or a group —CH$_2$—[pyridyl] or —CH$_2$SO$_2$—[phenyl], and X and Y are N—CN or O, with the proviso that at least one of X or Y must be N—CN.

2. A pyrrolo[3,4-c]pyrrole according to claim 1, wherein A and B are each independently of the other a group of formula

[structures shown with $R_1$, $R_2$; naphthyl; pyridyl N; and phenyl-G-phenyl with $R_3$, $R_4$]

wherein $R_1$ and $R_2$ are each independently of the other hydrogen, chloro, bromo, $C_1$–$C_4$alkyl, $C_1$–$C_6$alkoxy, $C_1$–$C_6$alkylamino, CN or phenyl, $R_3$ and $R_4$ are hydrogen, and G is —O—, —NR$_7$—, —N=N— or —SO$_2$—, wherein $R_7$ is hydrogen, methyl or ethyl.

3. A pyrrolo[3,4-c]pyrrole according to claim 1, wherein A and B in formula I are identical.

4. A pyrrolo[3,4-c]pyrrole according to claim 1, wherein A and B in formula I are a group of formula

[phenyl with $R_1$, $R_2$]

wherein $R_1$ and $R_2$ are each independently of the other hydrogen, methyl, tert-butyl, chloro, bromo, CN or phenyl.

5. A pyrrolo[3,4-c]pyrrole according to claim 1, wherein D and E in formula I are identical and are $C_1$–$C_4$alkyl, unsubstituted or chloro-substituted phenyl, allyl or benzyl, or a group —COO—C(CH$_3$)$_3$, —COO—CH$_2$—[phenyl], —COO—CH$_2$—[pyridyl N] or —COO—CH$_2$SO$_2$—[phenyl].

6. A pyrrolo[3,4-c]pyrrole according to claim 5, wherein D and E in formula I are preferably $C_1$–$C_4$alkyl or a group —COO—C(CH$_3$)$_3$.

7. A pyrrolo[3,4-c]pyrrole according to claim 1, wherein X and Y in formula I are N—CN.

* * * * *